US012564362B2

(12) United States Patent (10) Patent No.: US 12,564,362 B2
Saito (45) Date of Patent: Mar. 3, 2026

(54) X-RAY CT DEVICE, DATA PROCESSING METHOD, AND STORAGE MEDIUM

(71) Applicant: CANON MEDICAL SYSTEMS CORPORATION, Otawara (JP)

(72) Inventor: Yasuo Saito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 185 days.

(21) Appl. No.: 18/530,337

(22) Filed: Dec. 6, 2023

(65) Prior Publication Data

US 2024/0188910 A1 Jun. 13, 2024

(30) Foreign Application Priority Data

Dec. 8, 2022 (JP) ................................. 2022-196281

(51) Int. Cl.
*A61B 6/40* (2024.01)
*A61B 6/00* (2024.01)
*A61B 6/03* (2006.01)
(52) U.S. Cl.
CPC .............. *A61B 6/405* (2013.01); *A61B 6/032* (2013.01); *A61B 6/481* (2013.01)

(58) Field of Classification Search
CPC ......... A61B 6/405; A61B 6/032; A61B 6/481; A61B 6/4241; A61B 6/542; A61B 6/482
See application file for complete search history.

(56) References Cited

U.S. PATENT DOCUMENTS

2017/0020472 A1* 1/2017 Eusemann ............. A61B 6/463
2022/0096028 A1 3/2022 Gatayama et al.

FOREIGN PATENT DOCUMENTS

JP 2022-57301 A 4/2022

* cited by examiner

*Primary Examiner* — Courtney D Thomas
(74) *Attorney, Agent, or Firm* — Oblon, McClelland, Maier & Neustadt, L.L.P.

(57) ABSTRACT

An X-ray CT device of an embodiment includes processing circuitry. The processing circuitry acquires data corresponding to energy when X-rays radiated by an X-ray tube are transmitted through a subject. The processing circuitry adjusts conditions including first and second conditions for the data when the data is acquired. The processing circuitry switches the condition from the first condition to the second condition when an injection state of a contrast agent injected into the subject satisfies a predetermined condition. The processing circuitry bundles the data discriminated into some of a plurality of energy bins.

11 Claims, 7 Drawing Sheets

FIG. 3

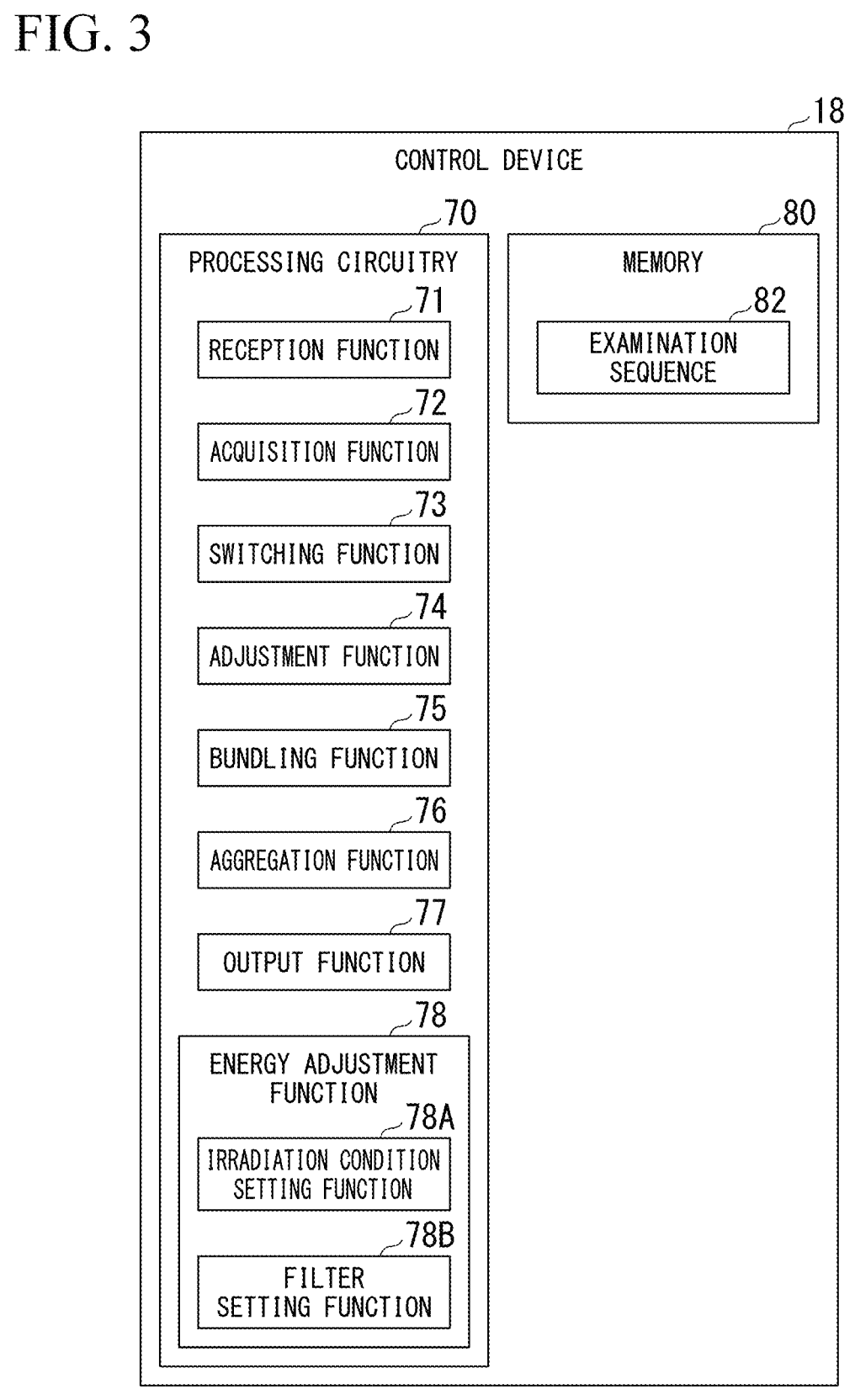

CONTROL DEVICE — 18

PROCESSING CIRCUITRY — 70

- RECEPTION FUNCTION — 71
- ACQUISITION FUNCTION — 72
- SWITCHING FUNCTION — 73
- ADJUSTMENT FUNCTION — 74
- BUNDLING FUNCTION — 75
- AGGREGATION FUNCTION — 76
- OUTPUT FUNCTION — 77
- ENERGY ADJUSTMENT FUNCTION — 78
  - IRRADIATION CONDITION SETTING FUNCTION — 78A
  - FILTER SETTING FUNCTION — 78B

MEMORY — 80

- EXAMINATION SEQUENCE — 82

Figure 4:
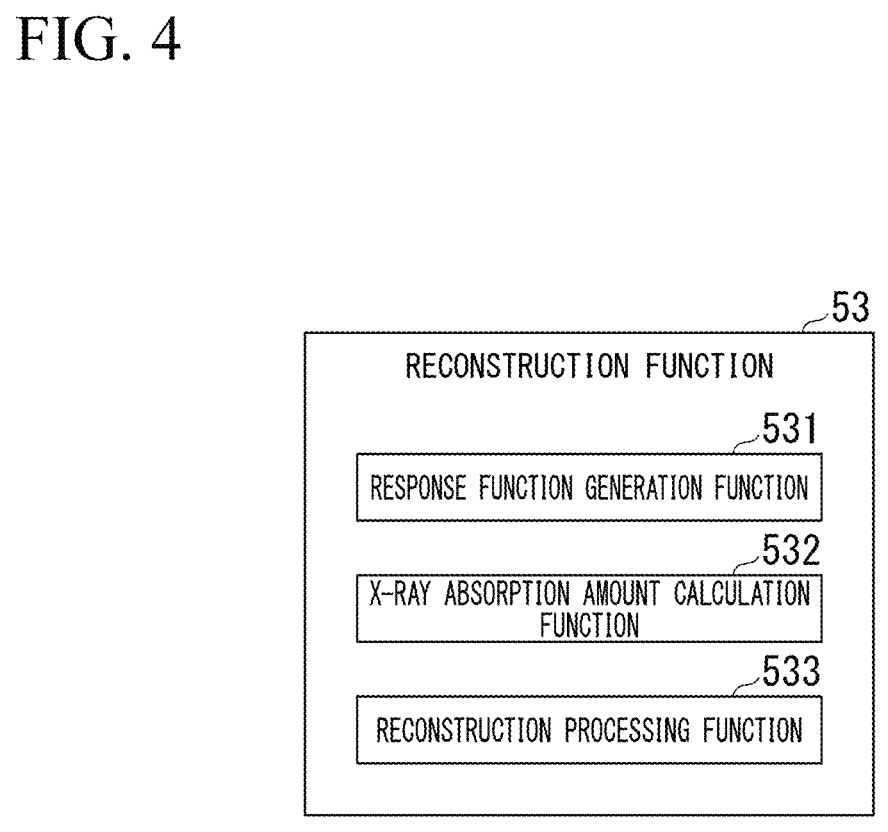

RECONSTRUCTION FUNCTION

531

RESPONSE FUNCTION GENERATION FUNCTION

532

X-RAY ABSORPTION AMOUNT CALCULATION FUNCTION

533

RECONSTRUCTION PROCESSING FUNCTION

FIG. 6

| SWITCHING TIME | LONG | SHORT |
|---|---|---|
| SWITCHING METHOD | BIN BUNDLING METHOD (MULTI-ENERGY-BIN MODE) | SINGLE-ENERGY-BIN MODE → MULTI-ENERGY-BIN MODE |

ACQUISITION

BUNDLING

RECONSTRUCTION

DAS PRE-BUNDLING
PROCESS
LOW RAY DOSE

DAS POST-BUNDLING
PROCESS
SINGLE-ENERGY-BIN MODE
:LOW RAY DOSE
MULTI-ENERGY-BIN MODE
:HIGH RAY DOSE

SINGLE-ENERGY-BIN MODE

MULTI-ENERGY-BIN MODE

1    #2    #3    #4

X-RAY CT DEVICE, DATA PROCESSING METHOD, AND STORAGE MEDIUM

CROSS-REFERENCE TO RELATED APPLICATION

The present application claims priority based on Japanese Patent Application No. 2022-196281, filed Dec. 8, 2022, the content of which is incorporated herein by reference.

FIELD

Embodiments and drawings disclosed herein relate to an X-ray computed tomography (CT) device, a data processing method, and a storage medium.

BACKGROUND

As an imaging method using an X-ray CT device, there is a method called RealPrep for starting imaging when a predetermined amount of contrast agent flows into a region of interest (ROI) such as an organ including human tissues. Also, as the X-ray CT device, a so-called photon-counting CT device that acquires data obtained by counting the number of X-ray photons for energy, is known and may be used in real-time.

A photon-counting CT device processes huge amounts of data with a detector that counts the number of X-ray photons. For this reason, because the amount of data to be transmitted is also enormous, real-time transmission is difficult. Therefore, it may be difficult to generate an image required by a surgeon during the manipulation in the photon-counting CT device for use in RealPrep.

BRIEF DESCRIPTION OF THE DRAWINGS

FIG. 3 is a diagram showing an example of a part of a configuration of a control device according to the embodiment.

FIG. 4 is a diagram showing an example of a functional block of a reconstruction function according to the embodiment.

FIG. 6 is a flowchart showing another example of the process of the control device according to the embodiment.

DETAILED DESCRIPTION

Hereinafter, an X-ray CT device, a data processing method, and a storage medium of embodiments will be described with reference to the drawings.

An X-ray CT device of an embodiment includes processing circuitry. The processing circuitry acquires data corresponding to energy when X-rays radiated by an X-ray tube are transmitted through a subject. The processing circuitry adjusts conditions including first and second conditions for the data when the data is acquired. The processing circuitry switches the condition from the first condition to the second condition when an injection state of the contrast agent injected into the subject satisfies a predetermined condition. The processing circuitry bundles the data discriminated into some of a plurality of energy bins. Thereby, it is possible to reduce a transmission amount of data.

Figure 1:
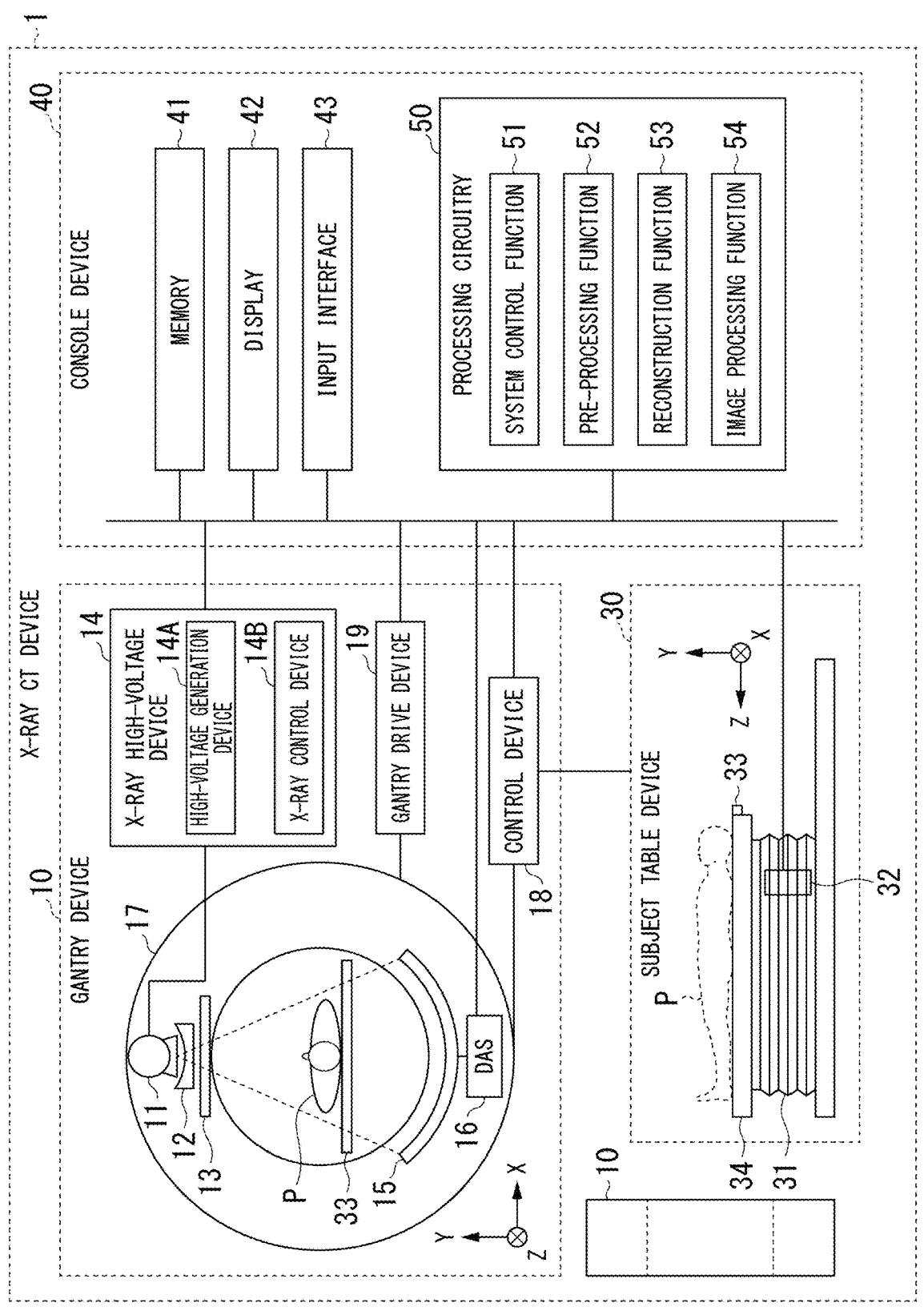
FIG. 1 is a diagram showing an example of an X-ray CT device according to an embodiment.

The X-ray CT device of the embodiment is a photon-counting CT device. The photon-counting CT device discriminates a substance through which X-rays are transmitted, for example, using a direct conversion type detector. The X-ray CT device of the embodiment is utilized when RealPrep is performed. RealPrep is a method of injecting a contrast agent into the subject and shifting the scan from a monitor scan to the main scan when the injection state satisfies a predetermined condition. As a predetermined condition, for example, a dyeing degree of the contrast agent or an injection amount of the contrast agent exceeds a threshold value. The dyeing degree of the contrast agent is expressed, for example, as a dyeing amount indicated by the X-ray absorption value. For example, the dyeing amount in a predetermined region exceeds the threshold value, so that the scan is shifted from the monitor scan to the main scan. FIG. 1 is a diagram showing an example of an X-ray CT device 1 according to the embodiment. The X-ray CT device 1 includes, for example, a gantry device 10, a subject table device 30, and a console device 40. Although both a view of the gantry device 10 seen from the Z-axis direction and a view of the gantry device 10 seen from the X-axis direction are shown, for the convenience of description, in FIG. 1, the actual number of gantry devices 10 is one. In the embodiment, a longitudinal direction of the rotation shaft of a rotation frame 17 or a top plate 33 of the subject table device 30 in a non-tilt state is defined as a Z-axis direction, an axis orthogonal to the Z-axis direction and horizontal to a floor surface is defined as an X-axis direction, and a direction orthogonal to the Z-axis direction and perpendicular to the floor surface is defined as a Y-axis direction.

The gantry device 10 includes, for example, an X-ray tube 11, a wedge 12, a collimator 13, an X-ray high-voltage device 14, an X-ray detector 15, a data acquisition system (hereinafter referred to as DAS) 16, a rotation frame 17, a control device 18, and a gantry drive device 19. The X-ray tube 11, the wedge 12, the collimator 13, the X-ray high-voltage device 14, the X-ray detector 15, the DAS 16, the rotation frame 17, and the control device 18 are housed in a housing. Input interfaces such as switches to be operated by an operator are provided in the housing. The rotation frame 17 rotatably holds the X-ray tube 11, the wedge 12, the collimator 13, and the X-ray detector 15. The rotation frame 17 may hold the X-ray detector 15, the DAS 16, and the control device 18.

The X-ray tube 11 generates X-rays by radiating thermal electrons toward a positive electrode (target) from a negative electrode (filament) according to the application of a high voltage from the X-ray high-voltage device 14. The X-ray tube 11 includes a vacuum tube. For example, the X-ray tube 11 is a rotating positive-electrode type X-ray tube that generates X-rays by radiating thermal electrons to the rotating positive electrode.

The wedge 12 is a filter for adjusting an X-ray dose radiated from the X-ray tube 11 to a subject P. The wedge 12 attenuates the X-rays transmitted through the wedge 12 so that a distribution of a dose of X-rays radiated from the X-ray tube 11 to the subject P is a predetermined distribution. The wedge 12 is also referred to as a wedge filter or a bow-tie filter. The wedge 12 is, for example, aluminum processed to have a predetermined target angle or a predetermined thickness. The wedge 12 includes a filter replacement device that replaces the filter with another type of filter according to, for example, a control process of the control device 18. The filter may be configured to include, for example, silver or tin.

The collimator 13 is a mechanism for narrowing down an irradiation range of X-rays transmitted through the wedge 12. The collimator 13, for example, narrows down the X-ray irradiation range by combining a plurality of lead plates and forming a slit. The collimator 13 may be referred to as an X-ray diaphragm. The collimator 13 includes a narrowing-down device that mechanically drives a narrowed-down range in, for example, the control process of the control device 18.

The X-ray high-voltage device 14 includes, for example, a high-voltage generation device 14A and an X-ray control device 14B. The high-voltage generation device 14A has electric circuitry including a transformer, a rectifier, and the like, and generates a high voltage to be applied to the X-ray tube 11. The X-ray control device 14B controls an output voltage (kV) (a voltage of electricity to be supplied to the X-ray tube 11) of the high-voltage generation device 14A and an electric current value (mA) to be supplied to the X-ray tube 11 in accordance with a dose of X-rays to be generated by the X-ray tube 11 in the control process of the control device 18. The high-voltage generation device 14A may boost a voltage with the above-described transformer or may boost a voltage with an inverter. The X-ray high-voltage device 14 may be provided on the rotation frame 17 or may be provided on the side of a fixed frame (not shown) of the 15 gantry device 10.

The X-ray detector 15 detects an intensity of the X-rays generated by the X-ray tube 11 and incident through the subject P. The X-ray detector 15 outputs an electrical signal (which may be an optical signal or the like) corresponding to the detected intensity of the X-rays to the DAS 16. The X-ray detector 15 has, for example, a plurality of X-ray detection element arrays. In each of the plurality of X-ray detection elements, for example, a plurality of X-ray detection elements are arrayed in a channel direction along an arc centered on the focus of the X-ray tube 11. The plurality of X-ray detection element arrays are arranged in a slice direction (a column direction or a row direction). In the X-ray detector 15, if a region where one unit of X-ray photons is detected is not spatially narrowed and if a plurality of X-ray photons enter one X-ray detection element at the same time, one photon having high energy and two photons having low energy may become indistinguishable. On the other hand, in one subpixel, a region may be too small and a detection signal may be too small to obtain a sufficient signal value due to S/N problems. For this reason, the X-ray detection element bundles a plurality of subpixels, for example, 3×3 subpixels, into one X-ray detection element.

The X-ray detector 15 is, for example, a direct conversion type detector. As the X-ray detector 15, for example, a semiconductor diode in which electrodes are attached to both ends of the semiconductor can be applied. X-ray photons incident on a semiconductor are converted into electron-hole pairs. The number of electron-hole pairs generated due to the incidence of one X-ray photon depends on the energy of the incident X-ray photon. Electrons and holes are each attracted to a pair of electrodes formed at both ends of the semiconductor. A pair of electrodes generates an electric pulse with a wave height value corresponding to the charge of the electron-hole pair. Each electric pulse has a wave height value corresponding to the energy of the incident X-ray photon. X-ray photons are an example of a substance.

For example, the DAS 16 acquires count data indicating the counted number of X-ray photons detected by the X-ray detector 15 with respect to a plurality of energy bins in accordance with a control signal from the control device 18. The count data relating to the plurality of energy bins corresponds to an energy spectrum relating to incident X-rays for the X-ray detector 15, which is modified in accordance with the response characteristics of the X-ray detector 15. The DAS 16 outputs detection data based on the digital signal to the control device 18. The detection data is data corresponding to the energy when the X-rays radiated by the X-ray tube 11 are transmitted through the subject P. The detection data is a digital value of the count data identified by a channel number of the X-ray detection element of a generation source, a column number, and a view number indicating an acquired view. The view number is a number that changes with the rotation of the rotation frame 17, and is, for example, a number that is incremented in accordance with the rotation of the rotation frame 17. Accordingly, the view number is information indicating a rotation angle of the X-ray tube 11. A view period is a period that falls between a rotation angle corresponding to a certain view number and a rotation angle corresponding to the next view number. The DAS 16 may detect the switching of view from a timing signal input from the control device 18, may detect the switching of view with an internal timer, or may detect the switching of view from a signal acquired from a sensor (not shown). In the case where X-rays are continuously exposed by the X-ray tube 11 when a full scan is performed, the DAS 16 acquires a detection data group for the entire perimeter (360 degrees). In the case where X-rays are continuously exposed by the X-ray tube 11 when a half-scan is performed, the DAS 16 acquires detection data for half a perimeter (180 degrees).

Figure 2:
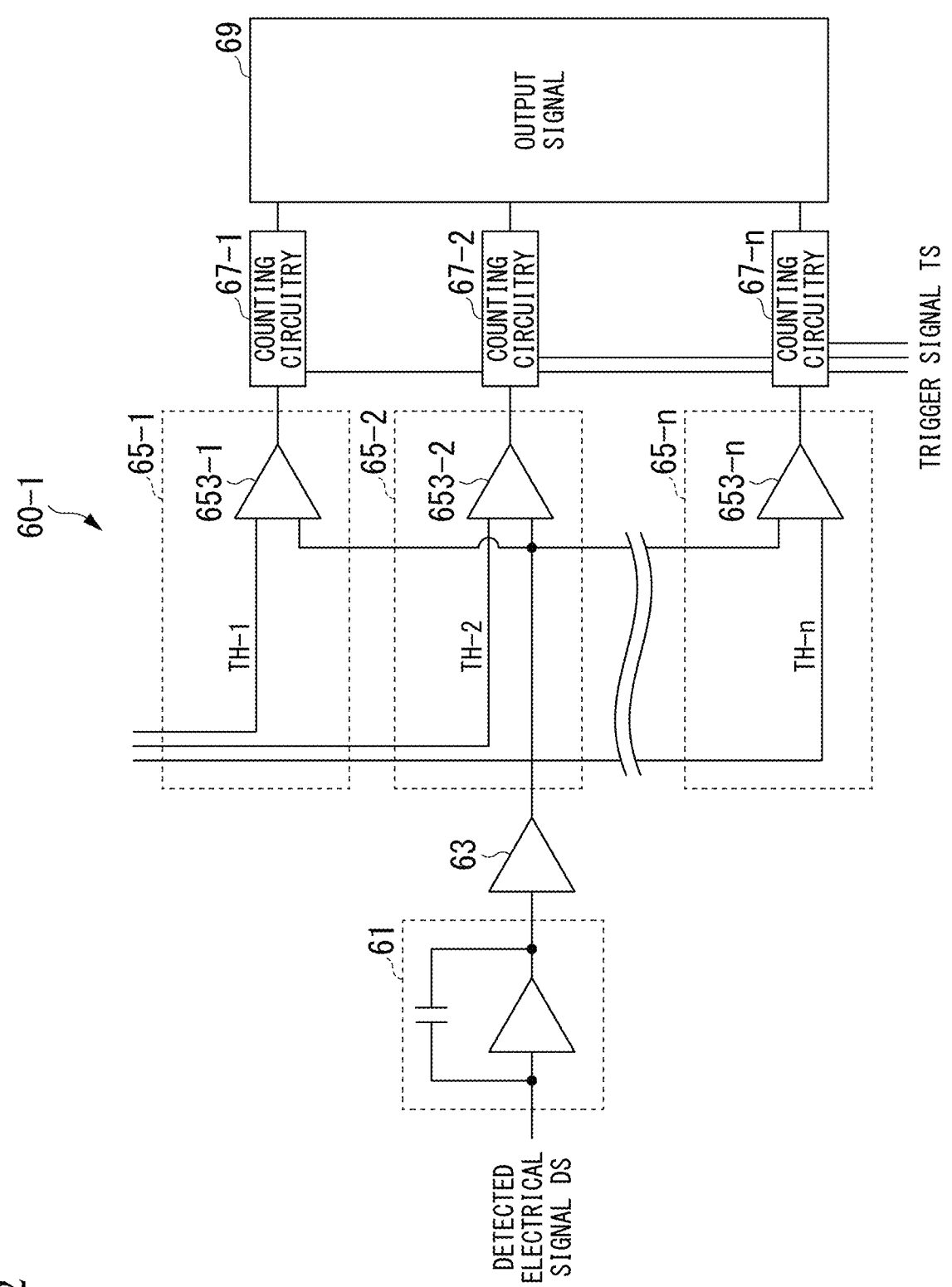
FIG. 2 is a diagram showing an example of a configuration of a data acquisition system (DAS) according to the embodiment.

FIG. 2 is a diagram showing an example of the configuration of the DAS 16 according to the embodiment. The DAS 16 includes read channels for the number of channels corresponding to the number of X-ray detection elements. These read channels are mounted in parallel in an integrated circuit such as an application-specific integrated circuit (ASIC). In FIG. 2, only a configuration of a DAS 16-1 for one read channel is shown.

The DAS 16-1 includes preamplifier circuitry 61, waveform shaping circuitry 63, a plurality of pieces of wave height discrimination circuitry 65, a plurality of pieces of counting circuitry 67, and output circuitry 69. The preamplifier circuitry 61 amplifies a detected electrical signal DS (an electric current signal) from an X-ray detection element of a connection destination. For example, the preamplifier circuitry 61 converts an electric current signal from the X-ray detection element of the connection destination into a voltage signal having a voltage value (a wave height value) proportional to a charge amount of the electric current signal. The waveform shaping circuitry 63 is connected to the preamplifier circuitry 61. The waveform shaping circuitry 63 shapes a waveform of a voltage signal from the preamplifier circuitry 61. For example, the waveform shaping circuitry 63 reduces a pulse width of the voltage signal from the preamplifier circuitry 61.

A plurality of counting channels corresponding to the number of energy bands (energy bins) are connected to the waveform shaping circuitry 63. When n energy bins are set, n counting channels are provided in the waveform shaping circuitry 63. Each counting channel has wave height discrimination circuitry 65-*n* and counting circuitry 67-*n*.

Each of the pieces of the wave height discrimination circuitry 65-*n* discriminates the energy of X-ray photons detected by the X-ray detection element at the wave height value of the voltage signal from the waveform shaping circuitry 63. For example, the wave height discrimination circuitry 65-n includes comparison circuitry 653-n. A voltage signal from the waveform shaping circuitry 63 is input to one input terminal of each of pieces of the comparison circuitry 653-n. A reference signal TH (reference voltage value) corresponding to a different threshold value is supplied from the control device 18 to the other input terminal of each of pieces of the comparison circuitry 653-n. For example, a reference signal TH-1 is supplied to comparison circuitry 653-1 for an energy bin bin1, a reference signal TH-2 is supplied to comparison circuitry 653-2 for an energy bin bin2, and a reference signal TH-n is supplied to comparison circuitry 653-n for an energy bin binn. Each of the reference signals TH has an upper limit reference value and a lower limit reference value. Each of pieces of the comparison circuitry 653-n outputs an electric pulse signal when the voltage signals from the waveform shaping circuitry 63 have a wave height value corresponding to the energy bin corresponding to each of the reference signals TH. For example, the comparison circuitry 653-1 outputs an electric pulse signal when the wave height value of the voltage signal from the waveform shaping circuitry 63 is the wave height value corresponding to the energy bin bin1 (when the wave height value is between the reference signals TH-1 and TH-2). On the other hand, the comparison circuitry 653-1 for the energy bin bin1 does not output an electric pulse signal when the wave height value of the voltage signal from the waveform shaping circuitry 63 is not the wave height value corresponding to the energy bin bin1. Also, for example, the comparison circuitry 653-2 outputs an electric pulse signal when the wave height value of the voltage signal from the waveform shaping circuitry 63 is a wave height value corresponding to the energy bin bin2 (reference signals TH-2 and TH-3).

The counting circuitry 67-n counts the electric pulse signal from the wave height discrimination circuitry 65-n at a read cycle that matches a view switching cycle. For example, the counting circuitry 67-n is supplied with a trigger signal TS from the control device 18 at each view switching timing. With the supply of the trigger signal TS as a trigger, the counting circuitry 67-n adds 1 to the count number stored in an internal memory every time an electric pulse signal is input from the wave height discrimination circuitry 65-n. With the supply of the next trigger signal as a trigger, the counting circuitry 67-n reads count number data (i.e., count data) stored in the internal memory and supplies the count data to the output circuitry 69. Also, the counting circuitry 67-n resets the count number stored in the internal memory to an initial value every time the trigger signal TS is supplied. In this way, the counting circuitry 67-n counts the count number for each view.

The output circuitry 69 is connected to the counting circuitry 67-n for a plurality of read channels mounted in the X-ray detector 15. The output circuitry 69 generates count data for a plurality of read channels for each view by integrating count data from the counting circuitry 67-n for a plurality of read channels for each of the plurality of energy bins. The count data of each energy bin is a collection of count data defined by a channel, a segment (column), and an energy bin. The count data of each energy bin is transmitted to the console device 40 in view units. The count data for each view unit is referred to as a count dataset CS.

Returning to FIG. 1, the rotation frame 17 is an annular member that faces and supports the X-ray tube 11, the wedge 12, the collimator 13, and the X-ray detector 15. The rotation frame 17 is rotatably supported by the fixed frame around the subject P introduced inside. The rotation frame 17 further supports the DAS 16. The detection data output by the DAS 16 is transmitted from a transmitter having a light emitting diode (LED) provided in the rotation frame 17 to a receiver having a photodiode provided in a non-rotating portion (for example, the fixed frame) of the gantry device 10 through optical communication and transferred to the console device 40 by the receiver. In addition, the method of transmitting detection data from the rotation frame 17 to the non-rotating portion is not limited to the above-described method using optical communication, and any non-contact type transmission method may be employed. As long as the rotation frame 17 can be rotated in support of the X-ray tube 11 or the like, it is not limited to an annular member and may be a member such as an arm.

Although the X-ray CT device 1 includes, for example, a Rotate/Rotate-Type X-ray CT device (third generation CT) in which both the X-ray tube 11 and the X-ray detector 15 are supported by the rotation frame 17 and rotate around the subject P, it is not limited thereto and may be a Stationary/Rotate-type X-ray CT device (fourth generation CT) in which a plurality of X-ray detection elements arrayed in a circular shape are fixed to the fixed frame and the X-ray tube 11 rotates around the subject P.

The control device 18, for example, has processing circuitry having a processor such as a CPU. The control device 18 receives an input signal from the input interface or the console device 40 attached to the gantry device 10 and controls operations of the gantry device 10, the subject table device 30, and the DAS 16. For example, the control device 18 controls the gantry drive device 19 so that the rotation frame 17 is allowed to rotate or the gantry device 10 is allowed to tilt. When the gantry device 10 is tilted, the control device 18 controls the gantry drive device 19 on the basis of a tilt angle input to the input interface and causes the rotation frame 17 to rotate around an axis parallel to a Z-axis direction. The control device 18 ascertains the rotation angle of the rotation frame 17 according to the output of a sensor (not shown) or the like. Also, the control device 18 provides the rotation angle of the rotation frame 17 to the reconstruction function 53 and the like as needed. Also, the control device 18 controls the energy bin (reference signal TH) of the DAS 16. The control device 18 may be provided in the gantry device 10 or in the console device 40.

The control device 18 discriminates and acquires the detection data output by the DAS 16, outputs the acquired detection data to the console device 40, or stores the acquired detection data in the storage device. FIG. 3 is a diagram showing an example of a part of the configuration of the control device 18 according to the embodiment. In FIG. 3, the configuration of the processing circuitry 70 and the memory 80 relating to the function of controlling the DAS 16 in the control device 18 is shown.

The processing circuitry 70 includes, for example, a reception function 71, an acquisition function 72, a switching function 73, an adjustment function 74, a bundling function 75, an aggregation function 76, an output function 77, and an energy adjustment function 78. In the processing circuitry 70, for example, these components are implemented, for example, by a hardware processor (a computer) executing a program (software) stored in the memory 41. The hardware processor is, for example, circuitry such as a central processing unit (CPU), a graphics processing unit (GPU), an application-specific integrated circuit (ASIC), or a programmable logic device (for example, a simple programmable logic device (SPLD), a complex programmable logic device (CPLD), or a field programmable gate array (FPGA)). Instead of storing the program in the memory 41, the program may be configured to be directly embedded in the circuitry of the hardware processor. In this case, the hardware processor implements each function by reading and executing the program embedded in the circuitry. The hardware processor is not limited to being configured as single circuitry and may be configured as one hardware processor by combining a plurality of pieces of independent circuitry to implement each function. Also, a plurality of components may be integrated into one hardware processor to implement each function.

The reception function 71 is performed to receive various types of information transmitted by the input interface provided in the gantry device 10 or the console device 40. The reception function 71 is an example of a reception portion. The information transmitted by the input interface or the console device 40 includes, for example, examination sequence information that defines a sequence until the scan is shifted from the monitor scan to the main scan with respect to RealPrep. The examination sequence includes a time threshold value serving as a criterion for determining the dyeing amount to shift the scan from the monitor scan to the main scan or a time threshold value serving as a criterion for adjusting the first condition and the second condition serving as a condition for the detection data when the detection data is acquired.

The first condition is a condition set when the acquisition mode is the first mode and the second condition is a condition set when the acquisition mode is the second mode. In the acquisition mode, the first mode is, for example, a mode set during the monitor scan in RealPrep and is a mode in which an amount of data transmitted in real-time by the output function 77 is limited.

The second mode is, for example, a mode set during the main scan in RealPrep, and is a mode in which the amount of data transmitted in real-time by the output function 77 is not limited or a limit amount is small. "Real-time" refers to a case where time exactly matches and some deviation is allowed for the delay time varying with the purpose of use.

The acquisition function 72 is performed to acquire detection data that is data corresponding to the energy of a substance, for example, an X-ray photon. The acquisition function 72 is performed to acquire, for example, detection data output by the DAS 16 as detection data. The acquisition function 72 is performed to store acquired detection data in the memory 80. The acquisition function 72 is an example of an acquisition portion.

The switching function 73 is performed to switch the acquisition mode during RealPrep between the first mode and the second mode on the basis of an examination sequence 82 transmitted by the console device 40 or the input interface provided in the housing and stored in memory 80. The switching function 73 is performed to substantially switch the condition for the detection data between the first condition and the second condition by switching the acquisition mode between the first mode and the second mode. The switching function 73 is an example of a switching portion.

The first mode of the acquisition mode is, for example, a mode in which the number of energy bins is small, for example, the number of energy bins is set to only one, and the number of X-ray photons of a wide numerical standard (wave height value range) is counted in one energy bin. In the first mode, detection data is acquired in an energy bin mode (hereinafter referred to as a single-energy-bin mode) in which data corresponding to the energy of X-rays in one energy range is acquired or an energy bin mode (hereinafter referred to as a multi-energy-bin mode) in which detection data to be aggregated in one energy range or data corresponding to the energy of X-rays in a plurality of energy ranges is acquired. The number of energy bins set in the first mode may be two or more as long as it is less than the number of energy bins set in the second mode. The energy range is, for example, the range of the wave height value.

The second mode of the acquisition mode is a mode in which the large number of energy bins is set and the number of X-ray photons is counted in energy bins that are finely segmented into narrow numerical standards. Although detection data acquisition is often performed in the multi-energy-bin mode in the second mode, the detection data acquisition may be performed in the single-energy-bin mode. The switching function 73 may be performed to switch the acquisition mode on the basis of, for example, mode setting information transmitted by the input interface or the console device 40.

The adjustment function 74 is performed to adjust the condition for the detection data when the detection data is acquired on the basis of the acquisition mode to be switched by the switching function 73. The condition for the detection data is, for example, the number of energy bins for discriminating the detection data detected by the DAS 16. The adjustment function 74 is performed to adjust the number of energy bins to a number corresponding to the acquisition mode. The adjustment function 74 is an example of an adjustment portion.

The number of energy bins in the DAS 16 can be determined, for example, on the basis of an energy band of X-rays to be detected, its discrimination performance, and the like, and can be theoretically set to a large number such as 10 or more (hereinafter referred to as a first maximum value). On the other hand, even if the energy bin is set finely by improving the discrimination performance, the resolution in the X-ray detector may not be guaranteed. In this case, the significance of the fine energy bin setting is lowered. For this reason, the number of energy bins that can be clinically used as a device may be, for example, a number such as 5 or 6 (hereinafter referred to as a second maximum value).

The adjustment function 74 is performed to adjust the number of energy bins to a number less than the second maximum value in the first mode, for example, when the number of energy bins in the second mode is set to the second maximum value, on the basis of the idea of the first maximum value and the second maximum value. The adjustment function 74 may be performed to adjust the number of energy bins to a number less than the second maximum value in the first mode, for example, when the number of energy bins in the second mode is set to the second maximum value. The first mode of the embodiment is a mode in which the number of X-ray photons in the energy band capable of being detected in the second mode is all counted in one energy bin because the number of energy bins is set to one. The number of bins set in the second mode may be predetermined or may be determined on the basis of any condition.

The adjustment function 74, for example, may be performed to adjust the number of energy bins by adjusting a numerical standard relating to energy when detection data is discriminated. A numerical standard relating to energy is, for example, a range of wave height values when data is discriminated in an energy bin. Numerical standards are set in advance before the manipulation is performed for each of the first and second modes. Numerical standards may be able to be changed (adjusted) on the basis of information transmitted by the input interface or the console device 40.

The adjustment function 74 is performed to adjust an energy bin for bundling detection data in the bundling function 75 in accordance with a RealPrep situation. Specifically, the adjustment function 74 is performed to adjust an energy bin in accordance with the acquisition mode switched in the switching function 73. The adjustment function 74 is performed to adjust the number of energy bins to be bundled so that the first condition is satisfied when the monitor scan is being performed and the acquisition mode is the first mode. The adjustment function 74 is performed to adjust the number of energy bins to be bundled so that the second condition is satisfied when the acquisition mode is the second mode during the main scan.

The bundling function 75 is performed to bundle detection data discriminated into some of the plurality of energy bins. An energy bin with which the discriminated detection data is combined may be determined, for example, on the basis of mode setting information transmitted by the input interface or the console device 40 or mode setting information included in the scan plan. The bundling function 75 is an example of a bundling portion.

The aggregation function 76 is performed to aggregate the detection data bundled in the bundling function 75. The aggregation function 76 is performed to perform detection data aggregation (multi-energy-bin acquisition) by adding count data corresponding to the bundled detection data. In the following description, a process of bundling detection data in the bundling function 75 and a process of aggregating the detection data bundled in the bundling function 75 are referred to as a DAS post-bundling process.

When one energy bin is set in the first mode, a detection data bundling process of the bundling function 75 is not performed. In this case, the aggregation function 76 is performed to perform the detection data aggregation (single-energy-bin acquisition) as the count data included in one energy bin as it is. In the following description, the process of aggregating the detection data as the count data included in one energy bin as it is is referred to as a DAS pre-bundling process.

In addition, when a plurality of energy bins are set in the first mode, the DAS pre-bundling process includes a process of bundling detection data in the bundling function 75 and a process of aggregating detection data bundled in the bundling function 75 like the DAS post-bundling process. In this case, the number of energy bins when the DAS pre-bundling process is performed is adjusted to a number smaller than the number of energy bins when the DAS post-bundling process is performed.

For this reason, the number of detection data items aggregated in the DAS pre-bundling process is smaller than the number of detection data items aggregated in the DAS post-bundling process. Therefore, the burden on the control device 18 in the DAS pre-bundling process or the transmission amount of data transmitted from the control device 18 to the console device 40 is less (lighter) than that in the DAS post-bundling process.

The output function 77 is performed to output detection data aggregated in the aggregation function 76 to the console device 40 by transmitting the detection data thereto. For example, after detection data aggregated in the aggregation function 76 is output, the output function 77 is performed to output detection data stored in the memory 80. The output function 77 is an example of an output portion.

The energy adjustment function 78 is performed to control the wedge 12, the collimator 13, and the X-ray control device 14B so that the spectrum of X-rays irradiated by the X-ray tube 11 is adjusted, for example, when the monitor scan and the main scan are executed. The energy adjustment function 78, for example, is performed to control the wedge 12, the collimator 13, and the X-ray control device 14B so that the spectrum band is narrower when it is the first mode than when it is the second mode. The energy adjustment function 78, for example, is performed to control the wedge 12, the collimator 13, and the X-ray control device 14B so that the spectrum band is narrower when the monitor scan is performed than when the main scan is performed. The energy adjustment function 78 is an example of an energy adjustment portion.

The energy adjustment function 78 includes, for example, an irradiation condition setting function 78A and a filter setting function 78B. The irradiation condition setting function 78A, for example, is performed to transmit an irradiation condition setting signal to the X-ray control device 14B for setting an irradiation condition when X-rays are radiated by the X-ray tube 11. The irradiation conditions include, for example, an electric current value or a voltage value (kV) of electricity to be supplied to the X-ray tube 11 by the high-voltage generation device 14A, or both. The irradiation condition setting function 78A is an example of an irradiation condition setting portion.

Although the energy of the X-rays irradiated to the subject P can be adjusted by adjusting the voltage value or the electric current value of the electricity to be supplied to the X-ray tube 11, calibration is necessary because the spectral shape fluctuates when the voltage value is adjusted. On the other hand, when the electric current value is adjusted, calibration can be unnecessary because a change in the spectral shape is absent or extremely small.

The filter setting function 78B, for example, is performed to transmit a filter replacement signal for causing the filter replacement device to replace the filter to the wedge 12 or transmit a narrowing-down signal for adjusting a narrowed-down range by driving the narrowing-down device to the collimator 13. The filter setting function 78B is an example of a filter setting portion.

Each function included in the processing circuitry 70 may be provided within circuitry independent of the control device 18 that controls the operations of the gantry device 10, the subject table device 30, and the DAS 16 within the gantry device 10. For example, each function included in the processing circuitry 70 may be provided in conjunction with the DAS 16.

The memory 80 is implemented, for example, by semiconductor memory elements such as a random-access memory (RAM) and a flash memory, a hard disk, an optical disc, and the like. The memory 80 stores the detection data and the like aggregated in the aggregation function 76. The examination sequence 82 stored in the memory 80 is transmitted by the console device 40 or the input interface provided in the housing. The memory 80 is an example of a buffer.

Returning to FIG. 1, the gantry drive device 19 includes, for example, a motor and an actuator. The gantry drive device 19, for example, causes the rotation frame 17 to rotate or causes the gantry device 10 to tilt. The gantry drive device 19 causes the rotation frame 17 of the gantry device 10 to rotate on the basis of a tilt angle input to the input interface or a rotation instruction from the correction data acquisition function 57 to be described below.

The subject table device 30 is a device that places and moves the subject P to be scanned and introduces the subject P inside of the rotation frame 17 of the gantry device 10. The subject table device 30 includes, for example, a base 31, a subject table drive device 32, a top plate 33, and a support frame 34. The base 31 includes a housing that movably supports the support frame 34 in a vertical direction (a Y-axis direction). The subject table drive device 32 includes a motor and an actuator. The subject table drive device 32 causes the top plate 33 to move along the support frame 34 in a longitudinal direction (a Z-axis direction) of the top plate 33. Also, the subject table drive device 32 causes the top plate 33 to move in the vertical direction (the Y-axis direction). The top plate 33 is a plate-shaped member on which the subject P is placed.

The subject table drive device 32 may cause not only the top plate 33 but also the support frame 34 to move in the longitudinal direction of the top plate 33. Also, in contrast to the above, the gantry device 10 can be moved in the Z-axis direction, and the rotation frame 17 may be controlled so that the rotation frame 17 moves around the subject P by moving the gantry device 10. Also, both the gantry device 10 and the top plate 33 may have a configuration in which they can be moved. Also, the X-ray CT device 1 may be a device in which the subject P is scanned at a standing or sitting position. In this case, the X-ray CT device 1 has a subject support mechanism instead of the subject table device 30 and the gantry device 10 rotates the rotation frame 17 about an axial direction perpendicular to the floor surface.

The console device 40 includes, for example, a memory 41, a display 42, an input interface 43, and processing circuitry 50. Although the console device 40 separate from the gantry device 10 will be described in an embodiment, the gantry device 10 may include some or all of the components of the console device 40.

The memory 41 is implemented, for example, by semiconductor memory elements such as a RAM and a flash memory, a hard disk, an optical disc, and the like. The memory 41 stores, for example, detection data, projection data, reconstructed image data, CT image data, information about the subject P, an imaging condition, a correction data acquisition condition, and the like. The memory 41, for example, stores count data relating to a plurality of energy bins transmitted from the gantry device 10. The data may be stored in an external memory with which the X-ray CT device 1 can communicate in place of the memory 41 (or in addition to the memory 41). The external memory is controlled by a cloud server or the like, for example, when the cloud server that manages the external memory receives read and write requests.

The display 42 displays various types of information. For example, the display 42 displays a medical image (CT image) generated by processing circuitry, a graphical user interface (GUI) image for receiving various types of operations by an operator such as a doctor or a technician, and the like. The display 42 is, for example, a liquid crystal display, a cathode ray tube (CRT), an organic electroluminescence (EL) display, or the like. The display 42 may be provided in the gantry device 10. The display 42 may be a desktop type or a display device (for example, a tablet terminal) capable of performing wireless communication with the main body of the console device 40.

The input interface 43 receives various types of input operations by the operator and outputs an electrical signal indicating content of the received input operation to the processing circuitry 50.

For example, the input interface 43 is implemented by a mouse, a keyboard, a touch panel, a drag ball, a switch, button, a joystick, a camera, an infrared sensor, a microphone, and the like. The input interface 43 may be provided in the gantry device 10. Also, the input interface 43 may be implemented by a display device (for example, a tablet terminal) capable of performing wireless communication with the main body of the console device 40.

In addition, in the present specification, the input interface is not limited to those including physical operation parts such as a mouse or a keyboard. For example, electrical signal processing circuitry that receives an electrical signal corresponding to an input operation from an external input device provided separately from the device and outputs this electrical signal to control circuitry is also included in the example of the input interface.

The processing circuitry 50 controls the entire operation of the X-ray CT device 1, the operation of the gantry device 10, the operation of the subject table device 30, and the calibration operation for acquiring correction data. The processing circuitry 50 includes, for example, a system control function 51, a pre-processing function 52, a reconstruction function 53, an image processing function 54, and the like.

These components are implemented, for example, by a hardware processor (a computer) executing a program (software) stored in the memory 41. The hardware processor is, for example, circuitry such as a CPU, a GPU, an ASIC, or a programmable logic device (for example, an SPLD, a CPLD, or an FPGA). Instead of storing the program in the memory 41, the program may be configured to be directly embedded in the circuitry of the hardware processor.

In this case, the hardware processor implements each function by reading and executing the program embedded in the circuitry. The hardware processor is not limited to being configured as single circuitry and may be configured as one hardware processor by combining a plurality of pieces of independent circuitry to implement each function. Also, a plurality of components may be integrated into one hardware processor to implement each function.

Components provided in the console device 40 or the processing circuitry 50 may be decentralized and implemented by a plurality of pieces of hardware. The processing circuitry 50 may be implemented by a processing device capable of communicating with the console device 40 in place of the configuration of the console device 40. The processing device is, for example, a workstation connected to one X-ray CT device, or a device (for example, a cloud server) connected to a plurality of X-ray CT devices and configured to collectively execute processes equivalent to those of the processing circuitry 50 to be described below.

The system control function 51 is performed to control various types of functions of the processing circuitry 50 on the basis of the input operation received by the input interface 43.

The pre-processing function 52 is performed to generate projection data by performing pre-processing such as logarithmic conversion processing, offset correction processing, inter-channel sensitivity correction processing, beam hardening correction, scattered ray correction, and dark count correction on the detection data output by the DAS 16. The projection data includes count data.

The reconstruction function 53 is performed to reconstruct a photon-counting CT image of the subject P on the basis of the detection data (count data). FIG. 4 is a diagram showing an example of a functional block of the reconstruction function 53 according to the embodiment. The reconstruction function 53 is performed to include, for example, a response function generation function 531, an X-ray absorption amount calculation function 532, and a reconstruction processing function 533. The response function generation function 531 is performed to generate data of a response function indicating detector response characteristics. For example, the response function generation function 531 is performed to measure the response of a standard detection system (i.e., detection energy and detection intensity) to a plurality of monochromatic X-rays having a plurality of incident X-ray energies according to prediction calculations, experiments, and a combination of prediction calculations and experiments and generates a response function on the basis of measurement values of the detection energy and the detection intensity. Also, the response function generation function 531 may be configured to generate response function data on the basis of actually measured measurement values acquired in calibration and the like. The response function defines a relationship between the detection energy for each incident X-ray and the output response of the system. For example, the response function defines a relationship between the detection energy and the detection intensity for each incident X-ray. The data of the generated response function is stored in the memory 41.

The X-ray absorption amount calculation function 532 is performed to calculate an X-ray absorption amount for each of the plurality of base substances on the basis of the count data relating to the plurality of energy bins, an energy spectrum of the incident X-rays to the subject P, and a response function stored in the memory 41. The X-ray absorption amount calculation function 532 can be performed to calculate the X-ray absorption amount, which is not affected by the response characteristics of the X-ray detector 15 and the DAS 16, by calculating the X-ray absorption amount on the basis of the count data and the energy spectrum of the incident X-rays on the subject P using the response function. In this way, the process of obtaining an X-ray absorption amount for each base substance is also referred to as substance discrimination. All substances such as calcium, calcification, bone, fat, muscle, air, organs, lesions, hard tissues, soft tissues, and contrast substances can be set as the base substances. The type of base substance to be calculated may be determined in advance by an operator or the like via the input interface 43. The X-ray absorption amount indicates a dose of X-rays absorbed by the base substance. For example, the X-ray absorption amount is defined by a combination of an X-ray attenuation coefficient and an X-ray transmission path length.

The reconstruction processing function 533 is performed to reconstruct a photon counting type CT image that expresses a spatial distribution of the base substance to be imaged among the plurality of base substances on the basis of the X-ray absorption amount relating to each of the plurality of base substances calculated in the X-ray absorption amount calculation function 532 and causes the generated CT image data to be stored in the memory 41. The base substance to be imaged may be of one or more types. The type of base substance to be imaged may be determined by an operator or the like via the input interface 43.

The projection data including the count data obtained by the photon-counting CT device includes information of the energy of X-rays attenuated when the X-rays are transmitted through the subject P. For this reason, the reconstruction processing function 533, for example, can be performed to reconstruct CT image data of a specific energy component. Also, the reconstruction processing function 533, for example, can be performed to reconstruct CT image data for each of a plurality of energy components. Furthermore, the reconstruction processing function 533, for example, can be performed to assign a color tone corresponding to the energy component to each pixel of the CT image data of each energy component and generate image data in which a plurality of items of CT image data color-coded in accordance with the energy component are superimposed.

Returning to FIG. 1, the image processing function 54 is performed to generate a CT image such as three-dimensional image data or cross-sectional image data of any cross-section on the basis of the CT image data. The image processing function 54 may be performed to cause the display 42 to display the generated CT image. Conversion into three-dimensional image data may be performed in the pre-processing function 52.

According to the above-described configuration, the X-ray CT device 1 scans the subject P in a scan mode such as a helical scan, a conventional scan, or step-and-shoot. The helical scan is a mode in which the subject P is scanned in a spiral shape by rotating the rotation frame 17 while moving the top plate 33. The conventional scan is a mode in which the subject P is scanned in a circular trajectory by rotating the rotation frame 17 in a state in which the top plate 33 is stationary. The step-and-shoot is a mode in which the position of the top plate 33 is moved at regular intervals to perform the conventional scan in a plurality of scan areas.

Figure 5:
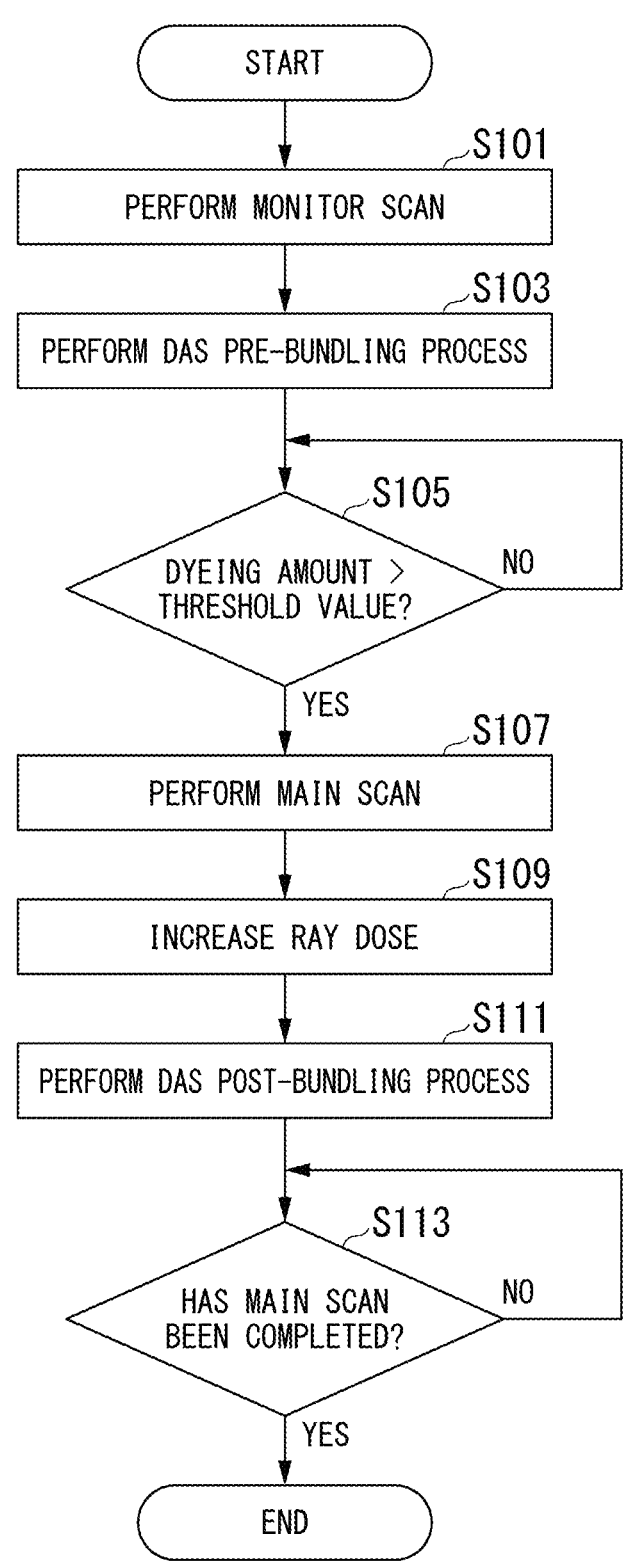
FIG. 5 is a flowchart showing an example of a process of a control device according to the embodiment.

Next, a process of the X-ray CT device 1 according to the embodiment will be described. FIG. 5 is a flowchart showing an example of a process in the control device 18 according to the embodiment. When RealPrep using the X-ray CT device 1 of the embodiment is started, the operator inputs an examination sequence by the input interface 43 in the console device 40. The console device 40 transmits the input examination sequence to the control device 18, and the control device 18 stores the received examination sequence in the memory 80. Subsequently, the X-ray CT device 1 starts the monitor scan (step S101).

The control device 18 sets the acquisition mode as the first mode in the processing circuitry 70 while the monitor scan is being performed and the adjustment function 74 is performed so that the DAS pre-bundling process of the bundling function 75 is performed when the aggregation function 76 is performed to aggregate the detection data (step S103). Here, in the first mode, instead of the DAS pre-bundling process, for example, detection data is acquired in the multi-energy-bin mode, and the number of energy bins in the DAS post-bundling process may be set to one or a smaller number.

The adjustment function 74 may be performed to match the energy bin mode in the monitor scan with, for example, the energy bin mode in the main scan. For example, when the acquisition function 72 is performed to acquire detection data in the single-energy-bin mode in the main scan, the adjustment function 74 may be performed to cause detection data to be acquired in the single-energy-bin mode even in the monitor scan in the acquisition function 72. If the number of energy bins is adjusted to one when it is a second condition in the present example, the adjustment function 74 is performed to adjust the number of energy bins to one even when it is the first condition. Also, when the acquisition function 72 is performed to acquire detection data in the multi-energy-bin mode in the main scan, the acquisition function 72 may be performed to perform a process of acquiring detection data in the multi-energy-bin mode in the monitor scan and setting the number of energy bins in the DAS post-bundling process to one or a smaller number.

While the monitor scan continues, the processing circuitry 70 determines whether or not a dyeing amount of a determination region serving as a determination target has exceeded a threshold value with reference to the examination sequence 82 stored in the memory 80 in the switching function 73 (step S105). The determination region here may be an organ itself serving as the examination target or may be a region other than the examination target. A region other than the examination target may be any region, for example, a predetermined region located on an upstream or downstream side of the examination target when a contrast agent is injected into the examination target. The dyeing amount included in the examination sequence may be any value, for example, an X-ray absorption value, an injection amount of a contrast agent, or an injection time of the contrast agent.

When it is determined that the dyeing amount of the determination region has not exceeded the threshold value, the switching function 73 is performed to iterate the processing of step S105. When it is determined that the dyeing amount in the determination region has exceeded the threshold value, the switching function 73 is performed to determine to shift the scan from the monitor scan to the main scan in RealPrep (step S107) and switch the acquisition mode from the first mode to the second mode.

When the acquisition mode is switched from the first mode to the second mode, the adjustment function 74 is performed to adjust the first condition and the second condition on the basis of the switching time. The switching time is determined, for example, on the basis of the time required to change the setting of the energy bin. FIG. 6 is a diagram showing a relationship between a switching time length and a switching method when the condition is switched between the first condition and the second condition. The switching time length, for example, is included and predefined in the examination sequence.

When the switching time is long and greater than or equal to the time threshold value, the adjustment function 74 uses a switching method which is a method of acquiring detection data in the multi-energy-bin mode in both the monitor scan and the main scan and switching the condition between the first condition and the second condition by only changing an energy bin bundling method. On the other hand, when the switching time is short and less than the time threshold value, the adjustment function 74 is performed to use a switching method which is a method of acquiring the detection data in the single-energy-bin mode in the monitor scan and acquiring the detection data in the multi-energy-bin mode in the main scan. The short switching time includes, for example, an extent to which the switching time does not matter in a particular protocol.

When the acquisition mode is switched to the second mode in the switching function 73, the energy adjustment function 78, for example, is performed to adjust the spectrum of X-rays radiated to the subject to a wide spectrum. For example, the energy adjustment function 78 is performed to transmit an irradiation condition setting signal in the irradiation condition setting function 78A to the X-ray control device 14B or transmit a filter replacement signal or a narrowing-down signal to the wedge 12 or the collimator 13 in the filter setting function 78B.

Subsequently, with the shift to the main scan in RealPrep, the switching function 73 is performed to switch the acquisition mode to the second mode and the adjustment function 74 performs the DAS post-bundling process (step S111). The processing circuitry 70 may store the acquired detection data in the memory 80 during the main scan. The detection data stored in the memory 80 may be output to an external device such as the console device 40 by the output function 77, for example, after RealPrep ends.

Subsequently, the switching function 73 is performed to determine whether or not the main scan in RealPrep has been completed (step S113). When it is determined that the main scan has not been completed, the switching function 73 is performed to iterate the processing of step S113. When it is determined in the switching function 73 that the main scan has not been completed, the control device 18 terminates the process shown in FIG. 5.

Figure 7:
FIG. 7 is a flowchart showing yet another example of the process of the control device according to the embodiment.
Figure 7:
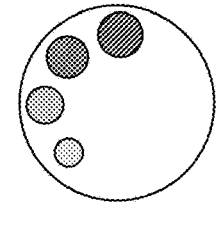
Figure 7:
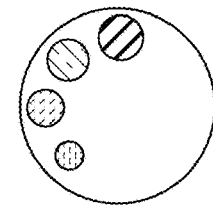
Figure 7:
Figure 7:
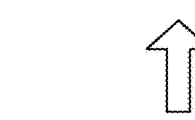
Figure 7:
Figure 7:
Figure 7:
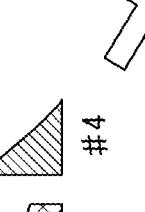
Figure 7:
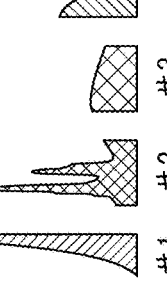
Figure 7:
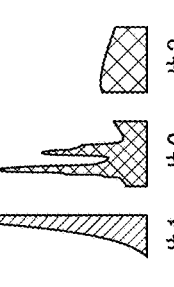

Here, in the DAS pre-bundling process and the DAS post-bundling process performed in the bundling function 75, a mode in which detection data is bundled will be described in the order of an acquisition step of acquiring the detection data, a bundling step of bundling the detection data, and a reconstruction step of reconstructing a CT image from the detection data. FIG. 7 is a diagram showing a procedure for bundling detection data in the bundling process. In FIG. 7, a histogram of detection data counted when the DAS pre-bundling process and the DAS post-bundling process are performed and the color state of the CT image generated in the reconstruction process are shown. The DAS pre-bundling process and the DAS post-bundling process are performed by the control device 18 and the reconstruction process is performed by the console device 40.

The distribution of detection data acquired in the acquisition step in the DAS pre-bundling process performed when the acquisition mode is mainly the first mode is indicated by a histogram covering the entire energy band without dividing the energy band. In the DAS pre-bundling process, the histogram indicated in the acquisition step is indicated as it is even in the bundling process.

In the DAS pre-bundling process, because the detection data is grouped into one, the transmission amount of detection data transmitted to the console device 40 is reduced. The detection data transmitted to the console device 40 is not distinguished by the energy band. For this reason, the CT image obtained by reconstructing the detection data generated in the DAS pre-bundling process is monochromatic.

On the other hand, in the acquisition step in the DAS post-bundling process performed when the acquisition mode is the first mode or the second mode, for example, the first to fourth energy bins #1 to #4 in which energy bands are defined are set as energy bins. In the acquisition step, the distribution of the detection data is indicated by a histogram divided into energy bands of the first to fourth energy bins #1 to #4. In the subsequent bundling process, the detection data included in the set energy bin is bundled to reduce the transmission amount of the detection data. The energy bin for bundling detection data, for example, varies with the acquisition mode. When the acquisition mode is the first mode, the energy bin mode is set to the single-energy-bin mode. In this case, the transmission amount of detection data can be greatly reduced by bundling the detection data of the first to fourth energy bins #1 to #4.

On the other hand, when the acquisition mode is the second mode, an energy bin for bundling detection data is set so that a detailed image can be generated in accordance with the request of the main scan. For this reason, the energy bin mode is set as the multi-energy-bin mode, and for example, detection data of the fourth energy bin #4 alone is set together with data obtained by bundling detection data of the first to third energy bins #1 to #3. Because the detection data transmitted to the console device 40 is divided into a portion corresponding to the first to third energy bins #1 to #3 and a portion corresponding to the fourth energy bin #4, the image obtained in reconstruction can be colored (or contrast to other parts can be increased).

The X-ray CT device 1 of the embodiment can switch the mode between the first mode and the second mode between the monitor scan in RealPrep and the main scan. For this reason, by using the single-energy-bin mode during the monitor scan, noise can be reduced compared to the main scan in which the multi-energy-bin mode is mainly used, the deterioration of the S/N ratio can be reduced, and the fastness when the CT image is generated can be ensured. Therefore, the transmission amount of data can be reduced. On the other hand, in the main scan mode, a detailed image can be generated in a multi-energy-bin mode or the like.

Also, when the switching time of the acquisition mode is long and greater than or equal to the time threshold value, the X-ray CT device 1 of the embodiment acquires detection data in the multi-energy-bin mode in both the monitor scan and the main scan and switches the condition between the first condition and the second condition by only changing the energy bin bundling method. For this reason, a period of time required for switching the acquisition mode can be reduced.

Also, the dose of X-rays radiated to the subject is lower during the monitor scan than during the main scan. For this reason, the radiation exposure of the subject when a CT image is generated during the monitor scan in which a detailed image as during the main scan is not required can be reduced.

According to at least one embodiment described above, the processing circuitry 70 acquires data corresponding to energy when X-rays radiated by an X-ray tube are transmitted through a subject. The processing circuitry 70 adjusts conditions including first and second conditions for the data when the data is acquired. The processing circuitry 70 switches the condition from the first condition to the second condition when an injection state of a contrast agent injected into the subject satisfies a predetermined condition. The processing circuitry 70 bundles the data discriminated into some of a plurality of energy bins. Thereby, it is possible to reduce a transmission amount of data.

While several embodiments of the present invention have been described above, these embodiments have been presented by way of example only, and are not intended to limit the scope of the inventions. These embodiments may be embodied in a variety of other forms. Various omissions, substitutions, and combinations may be made without departing from the spirit of the inventions. The inventions described in the accompanying claims and their equivalents are intended to cover such embodiments or modifications as would fall within the scope and spirit of the inventions.

What is claimed is:

1. An X-ray CT device comprising
processing circuitry configured to:
   acquire data corresponding to an energy when X-rays radiated by an X-ray tube are transmitted through a subject;
   adjust conditions including first and second conditions for the data when the data is acquired;
   switch a condition from the first condition to the second condition when an injection state of a contrast agent injected into the subject satisfies a predetermined condition; and
   bundle the data discriminated into some of a plurality of energy bins.

2. The X-ray CT device according to claim 1, wherein the processing circuitry further adjusts the energy of the X-rays to be radiated to the subject.

3. The X-ray CT device according to claim 2, wherein the processing circuitry adjusts a band of an X-ray spectrum to a narrower band when the condition is the first condition than when the condition is the second condition.

4. The X-ray CT device according to claim 2, wherein the processing circuitry further adjusts at least one of an electric current value and a voltage value of electricity to be supplied to the X-ray tube for radiating the X-rays.

5. The X-ray CT device according to claim 2, wherein the processing circuitry further sets a filter configured to adjust a dose of the X-rays to be radiated by the X-ray tube.

6. The X-ray CT device according to claim 1, wherein the processing circuitry adjusts the first condition and the second condition by changing a method of bundling a plurality of energy bins if a switching time when a switching portion switches the condition between the first condition and the second condition is less than a time threshold value.

7. The X-ray CT device according to claim 6, wherein the processing circuitry adjusts a number of energy bins to a smaller number when the condition is the first condition than when the condition is the second condition.

8. The X-ray CT device according to claim 6, wherein the processing circuitry adjusts a number of energy bins to one when the condition is the first condition.

9. The X-ray CT device according to claim 6, wherein the processing circuitry adjusts a number of energy bins to one even when the condition is the first condition if the processing circuitry adjusts the number of energy bins to one when the condition is the second condition.

10. A data processing method using a computer, the data processing method comprising:
   acquiring data corresponding to an energy when X-rays radiated by an X-ray tube are transmitted through a subject;
   adjusting conditions including first and second conditions for the data when the data is acquired;
   switching a condition from the first condition to the second condition when an injection state of a contrast agent injected into the subject satisfies a predetermined condition; and
   bundling the data discriminated into some of a plurality of energy bins.

11. A computer-readable non-transitory storage medium storing a program for causing a computer to:
   acquire data corresponding to an energy when X-rays radiated by an X-ray tube are transmitted through a subject;
   adjust conditions including first and second conditions for the data when the data is acquired;
   switch a condition from the first condition to the second condition when an injection state of a contrast agent injected into the subject satisfies a predetermined condition; and
   bundle the data discriminated into some of a plurality of energy bins.

* * * * *